United States Patent [19]

Berthold et al.

[11] Patent Number: 5,128,105
[45] Date of Patent: Jul. 7, 1992

[54] RACK SYSTEM FOR A PLURALITY OF SPECIMEN CONTAINERS FOR PERFORMING ASSAYS

[76] Inventors: Fritz Berthold, Eulerweg 9, D-7530 Pforzheim; Willy Lohr, Ginsterweg 75, D-7547 Wildbad, both of Fed. Rep. of Germany

[21] Appl. No.: 426,280

[22] Filed: Oct. 24, 1989

[30] Foreign Application Priority Data

Oct. 24, 1988 [DE] Fed. Rep. of Germany ....... 3836163

[51] Int. Cl.⁵ .................................................. B01L 9/00
[52] U.S. Cl. ........................................ 422/104; 422/65; 422/99; 422/102; 436/47; 436/48
[58] Field of Search ................... 422/65, 99, 102, 104; 436/97, 48

[56] References Cited

U.S. PATENT DOCUMENTS

| | | | |
|---|---|---|---|
| 3,713,771 | 1/1973 | Taylor et al. | 436/48 |
| 4,029,961 | 6/1977 | Lohr et al. | 250/328 |
| 4,168,955 | 9/1979 | Allington | 436/48 |
| 4,495,150 | 1/1985 | Cook et al. | 422/71 |
| 4,751,186 | 6/1988 | Baisch et al. | 422/102 |
| 4,895,650 | 1/1990 | Wang | 422/101 |

FOREIGN PATENT DOCUMENTS

| | | |
|---|---|---|
| 0039145 | 11/1981 | European Pat. Off. |
| 2448658 | 5/1975 | Fed. Rep. of Germany |
| 2529071 | 2/1976 | Fed. Rep. of Germany |
| 3623601 | 1/1988 | Fed. Rep. of Germany |

OTHER PUBLICATIONS

Woodhead, J. Stuart, PhD. and Ian Weeks, PhD, MRSC, "Chemiluminescence Immunoassay", Journal of Clinical Immunoassay, Spring 1984 (vol. 7, No. 1) pp. 82–89.

DeLuca, Marlene A. and William D. McElroy, "Bioluminescence and Chemiluminescence", Methods in Enzymology, 1986 (vol. 133), Academic Press, Inc., pp. 366–387.

Primary Examiner—Timothy M. McMahon
Attorney, Agent, or Firm—Spensley Horn Jubas & Lubitz

[57] ABSTRACT

A system for a plurality of specimen containers for performing assays, such as chemo- or bioluminescence measurements, includes a support element used for transporting the specimen containers through a measuring instrument, and a holder in which a plurality of specimen containers are received and which, for performing the measurement, can be mounted on the support element. The holder is a disposable component, so that once the measurement has been performed it can be discarded along with the specimen containers. For receiving multiple holders outside the measuring instrument, a stand is provided. Both on the holder and on the stand and support element, special provisions are made for positioning of the specimen containers both in the stand and in the support element in a way that both assures satisfactory measurement and precludes any mistake in the order of the specimen containers during the measurement or during the preparatory steps in the process. This system is suitable for performing chemiluminescence immunoassays, for instance.

19 Claims, 6 Drawing Sheets

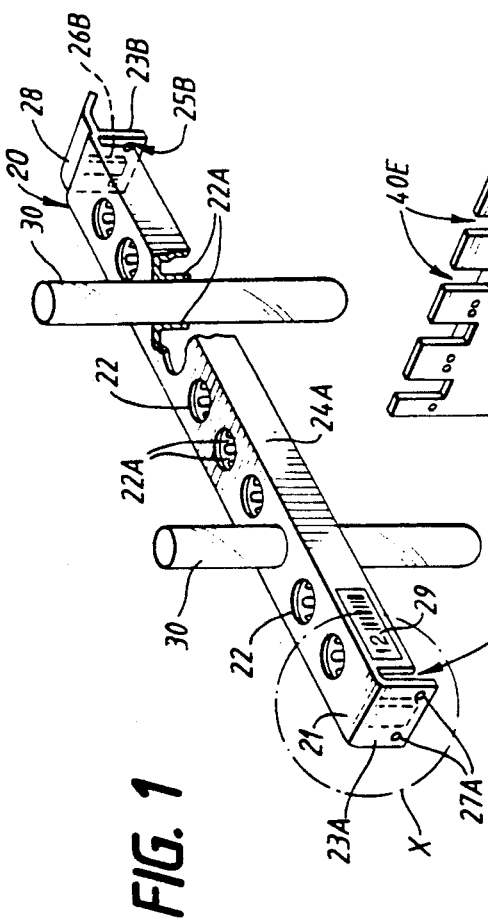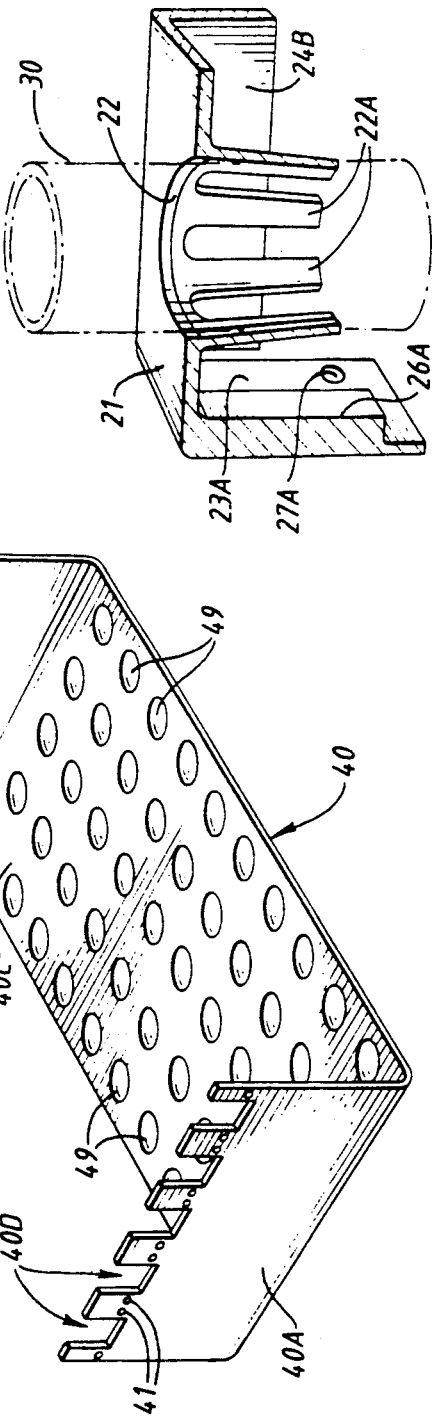

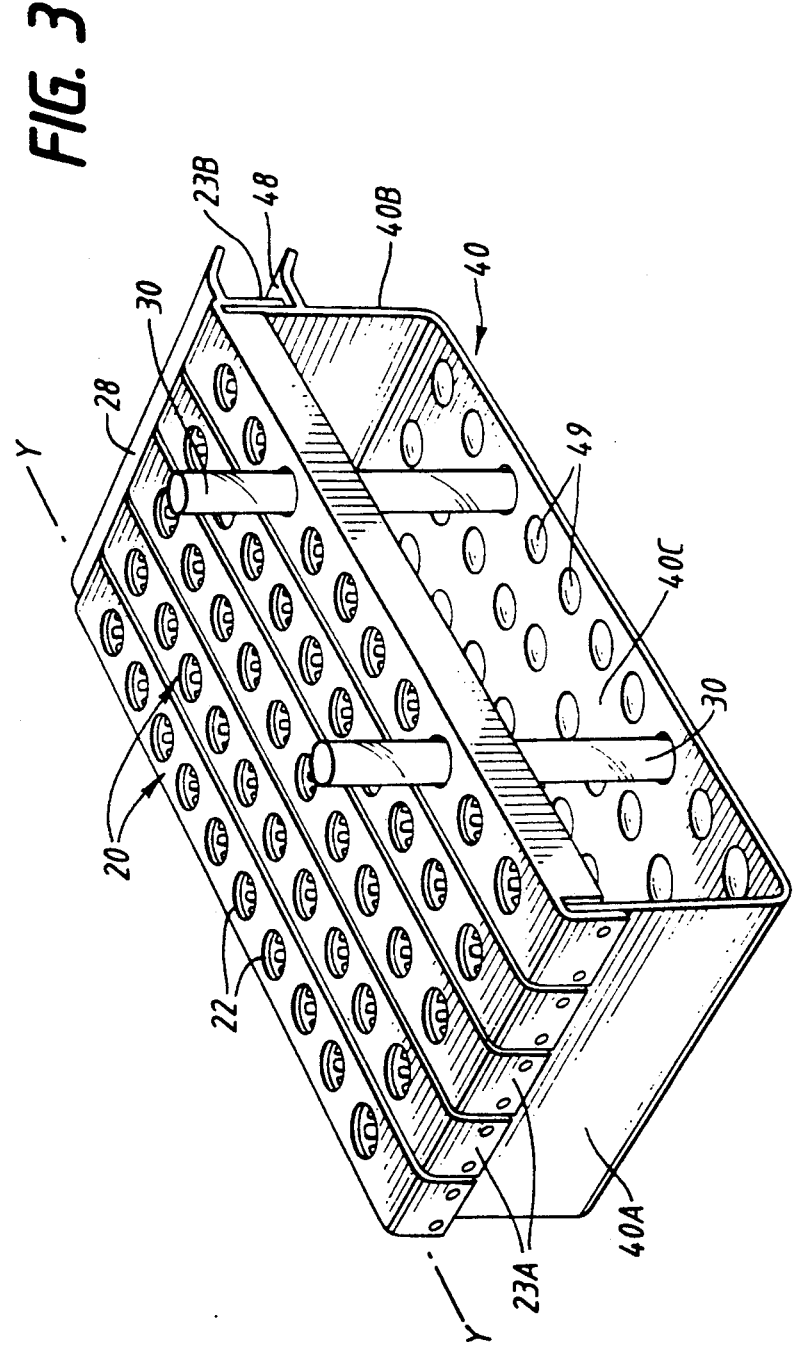

RACK SYSTEM FOR A PLURALITY OF SPECIMEN CONTAINERS FOR PERFORMING ASSAYS

BACKGROUND OF THE INVENTION

1. Field of the Invention.

The invention relates to a rack system for a plurality of specimen containers for use in performing assays such as chemo- or bioluminescence measurements in a measuring instrument in which, after procedures have been performed, the specimen containers in the rack are moved successively past a measurement site.

2. Prior Art.

Assays, such as measurements of chemiluminescence or bioluminescence, have gained considerable significance for the discovery or identification of certain substances, particularly in the medical field. Specialized techniques known as immunoassays are used for this purpose, based on the fact that for each of these substances (antigens, such as endogenous hormones or disease-causing microorganisms), a specific antibody can be associated with it, which may be present in the form of an endogenous immune substance or may be produced artificially. With the antigen to be detected, such a specific antibody forms a complex; if the antibody in turn is provided with a detectable marking, or label, then the presence of the applicable antigen can be detected by detecting this marking. The labeled antibody accordingly serves in a practical sense as a measuring sensor. Depending on the type and structure of the antigen and associated antibody, various immunoassays have been developed, which differ in the production of the thus-labeled antigen-antibody complex; an example is immunometric assays (for instance for detecting the TSH antigen), in which the antigen to be detected is first coupled to the associated, unlabeled antibody and subsequently the associated labeled antibody is coupled in turn to the antigen, forming a sandwich structure, with the result that the number of labels is approximately in proportion to the number of existing antigens to be detected.

This is contrasted by competitive assays, in which the antigens to be detected couple, in competition with labeled antigens, to a limited number of antibodies; the eventual result is that the number of labels decreases with the number of antigens to be detected.

Nonradioactive substances that can be induced to luminescence, such as acridinium ester molecules, have been increasingly used for the labeling, in which an exothermic reaction is initiated in the presence of hydrogen peroxide in alkaline solution, and the thermal energy of the reaction leads initially to the formation of excited molecular states; from these excited quantum states, the molecules then return (possibly with intermediate stops in between) to their basic state, and the energy difference between the quantum states is liberated in the form of photons, which can finally then be detected with the aid of a photomultiplier.

If such a label is used in immunoassays, such tests are consequently called chemiluminescence immunoassays. The basic features and details of such tests are explained for instance in the *Journal of Clinical Immunoassays*. Vol. 7, No. 1, 1984, pp. 82 ff, or *Methods of Enzymology*, Vol. 133, Part B, pp. 366 ff.

A common feature of all these immunoassays is that to perform them, a more or less large number of method steps is needed to achieve buildup of the aforementioned complex, that includes the label, from the specimen taken from the patient in which the applicable substance is to be detected. This takes place in stages including, among other steps, addition of the labeled antibodies or antigens, elimination of excess substances, and so forth.

As a rule, such measurement techniques are not performed, on a commercial laboratory scale, "individually", that is, by successive processing of a single specimen container; instead, batch quantities of up to a 100 sample containers are typical. The problem consequently arises of how to make a large number of sample containers, as a rule test tubes, proceed quickly and reliably, without any change in their order, through these method steps. Between method steps, the specimen containers must be shifted repeatedly among the various pieces of equipment involved, and finally must be moved into the measuring instrument.

It is accordingly typical for the specimen containers, optionally after suitable pretreatment, used for performing this kind of measurement, which is composed of a plurality of method steps, to be kept in a rack while as many method steps as possible can be carried out. In the simplest case, such a rack comprises a plastic stand having, for instance, a matrix of $5 \times 10$ holes on its top, into which the specimen containers are inserted.

For performing the actual measurement with a plurality of such test tubes, use may be made of a generic holder system for successive measurement of radioactively labeled specimens, such as described in U.S. Pat. No. 4,029,961. This system uses the so-called horizontal paternoster principle, in which a number of support elements, each holding a plurality of specimen containers, are moved successively past the measuring site. A holder that accommodates a plurality of specimen containers in a row is mounted on each support element. The specimen containers are retained by elastic plastic tongues of the holder until they reach the measuring position where the plastic tongues release the particular specimen container to be measured and that specimen container is then shifted vertically out of its holder to the actual measuring position.

German Published, Non-Examined patent application No. 25 29 071 shows a similar apparatus, in which plastic tongues extend under the bottom of the specimen containers. Because of the necessity of removing the specimen containers from their holders in their measuring position, this apparatus is necessarily complicated in structure and can be used only along with a support element adapted to it.

In the use of this rack system, the shifting of the specimen containers from the racks into the holders accordingly presents problems in that it is very time-consuming and is subject to mistakes caused by human error; particularly when such measuring methods are used in the medical field, such mistakes may possibly have grave consequences for the patient involved if there is an inaccurate diagnosis.

In another measuring instrument, disclosed in German Published, Non-Examined patent application No. 36 23 601, the specimen containers are inserted into holders placed against one another like links in a chain, which are moved continuously past the measuring site of the measuring instrument. Here the holders have lateral measuring openings, so that even in their respective measuring position the specimen containers can remain in the holders; although this arrangement allows structural simplification of the retaining tongues compared with the above-described systems, it is still unfeasible in the final analysis, because the holders themselves simultaneously also serve as the support element for carrying the specimen containers through the measuring instrument, and consequently must have a complicated structure. Hence the fundamental problem is still not solved; once again the specimen containers must be inserted individually into the holders and removed from them again after the measurement, since on the one hand the holders are too complicated and therefore too expensive to throw away, but on the other hand are difficult to clean.

A system in which the specimen containers can remain in position during the measurement and in which a separate support element on which the specimen containers can be mounted is used is disclosed in Published European Patent Document No. 0 039 145. In this system, however, clearly the advantage of ease attained because specimen containers need not be removed for the measurement procedure, is achieved at the cost of integrating 3×3 cuvettes into each holder, which means that once again the holders can necessarily be used only with a specific measuring instrument or support element designed for them. Moreover, the aforementioned advantage is due to the fact that measurement in the measuring instrument is performed vertically rather than horizontally; aside from the basic disadvantages of this measuring method, including a long path of radiation, and scattering effects caused by the bottom of the specimen containers, it is not possible to add reagents directly prior to the measurement, i.e., in the measuring position, because the space above the opening of the specimen containers is necessarily "occupied" by the detector head.

Accordingly this apparatus of European Patent Document No. 0 039 145 is not usable for measurements of the kind that require such an addition of reagents, or in other words for the immunoassays described at the outset above, where the luminescence of the label must be initiated immediately prior to the measurement. The resultant necessity for horizontal measurement, for which purpose the lateral measurement openings are provided in the manner disclosed in German Published, Non-Examined patent application No. 36 23 601, also precludes the use of holders having a matrix-like structure.

The system of European Patent Document No. 0 039 145 is therefore unusable for chemiluminescence and bioluminescence measurement.

German Published, Non-Examined patent application No. 24 48 658 discloses a holder for specimen containers that is intended both for holding a plurality of specimen containers and for passing them through the measurement site; similarly to the aforementioned German Published, Non-Examined patent application No. 36 23 601, this "integrated" version necessarily has a complicated structure, and consequently once again the specimen containers must be inserted individually for measurement and then removed again. In the measurement per se, specimens are aspirated from the test tubes; consequently no assays are performed. Since the holders have laterally closed receiving channels for the specimen containers, known as "holder pockets", the lateral openings or "holes" shown being intended not for measuring the specimens but rather solely for identifying individual holders using an optical reader, these holders are likewise unsuitable for performing chemiluminescence or bioluminescence measurements.

SUMMARY OF THE INVENTION

It is therefore an object of the invention to provide an improved a rack system for a plurality of specimen containers such that it can be used particularly for chemo- and bioluminescence measurements.

Another object of the invention is to achieve simplification of the entire procedural sequence, with maximum possible safety in handling, in that only a single holder is used as a component for all the method steps, on the one hand, and on the other hand the holder is structurally extremely simple.

The above and other objects are achieved, according to the present invention, by a system for holding a plurality of specimen containers, during performance of assays which are constituted by a sequence of procedures including a measurement procedure, in a measuring instrument having a measuring site at which the measurement procedure is performed, the system comprising: a support element specifically constructed to cooperate with the measuring instrument for moving the specimen containers successively past the measuring site; and a holder for holding a group of the specimen containers in a row, the holder comprising a plastic part having a longitudinal axis and provided with a group of container receiving openings spaced apart along the longitudinal axis for frictionally receiving the group of specimen containers, the plastic part having means for mounting the holder upon the support element in a defined position relative to the support element, wherein:

the support element comprises a housing having a longitudinal dimension, a top, a bottom and a group of receiving channels extending between the top and the bottom, opening at the top and spaced apart along the longitudinal dimension, each measuring channel being provided with a respective lateral measuring opening disposed at a location between the top and the bottom;

the channels are oriented and dimensioned to receive specimen containers held by the holder when the holder is mounted in the defined position upon the support element so that each specimen container will be in a defined position relative to an associated channel such that a region of each specimen container will be in registry with a respective lateral measuring opening; and the holder is a bracket-like disposable component in which a group of specimen containers can remain during all of the assay procedures, including the measurement procedure.

Accordingly a basic feature of the invention resides in the extremely suitable combination of two components in such a way that the support element is largely "instrument-specific", and in particular all the requirements, including provisions for carrying the system around, window openings, and so forth, needed for performing the actual measurement are met, while nevertheless the holder in which the specimen containers remain during all the stages in the procedure may be embodied as an inexpensive, "throwaway" plastic part, the purpose of which is merely to spatially arrange a number of specimen containers, and which, after the measurement is finished, can optionally be disposed of along with the specimen containers. Moreover, since the holder is made of a minimum of material, waste disposal problems associated therewith are minimized.

The specimen containers can be inserted into this holder at the outset and can remain there, thereby reliably avoiding tedious removal and replacement, which may cause mistakes and mixups, during all of the procedural and measurement steps.

By comparison, the support element can be adapted specifically to the particular measurement to be performed in the measuring instrument, for example by the suitable disposition of window openings for emission or extinction measurement. A support element embodied in this way may, for example, be used in a measuring instrument as described in the aforementioned U.S. Pat. No. 4,029,961.

An exemplary embodiment of a rack system according to the invention, and its handling, will now be described in further detail, with reference to the drawings.

BRIEF DESCRIPTION OF THE DRAWINGS

FIG. 1 is an exploded perspective view of the stand of an embodiment of a rack system according to the invention with an associated holder.

FIG. 2 is a detail view, partly in section, of a region designated by X in FIG. 1.

FIG. 3 is a view similar to that of FIG. 1 showing the stand of FIG. 1 with a plurality of holders mounted on it.

FIGS. 6A-6M are simplified pictorial illustrations of the sequence of steps in an immunoassay, using the elements of the rack system according to the invention.

DESCRIPTION OF THE PREFERRED EMBODIMENTS

Figure 4:
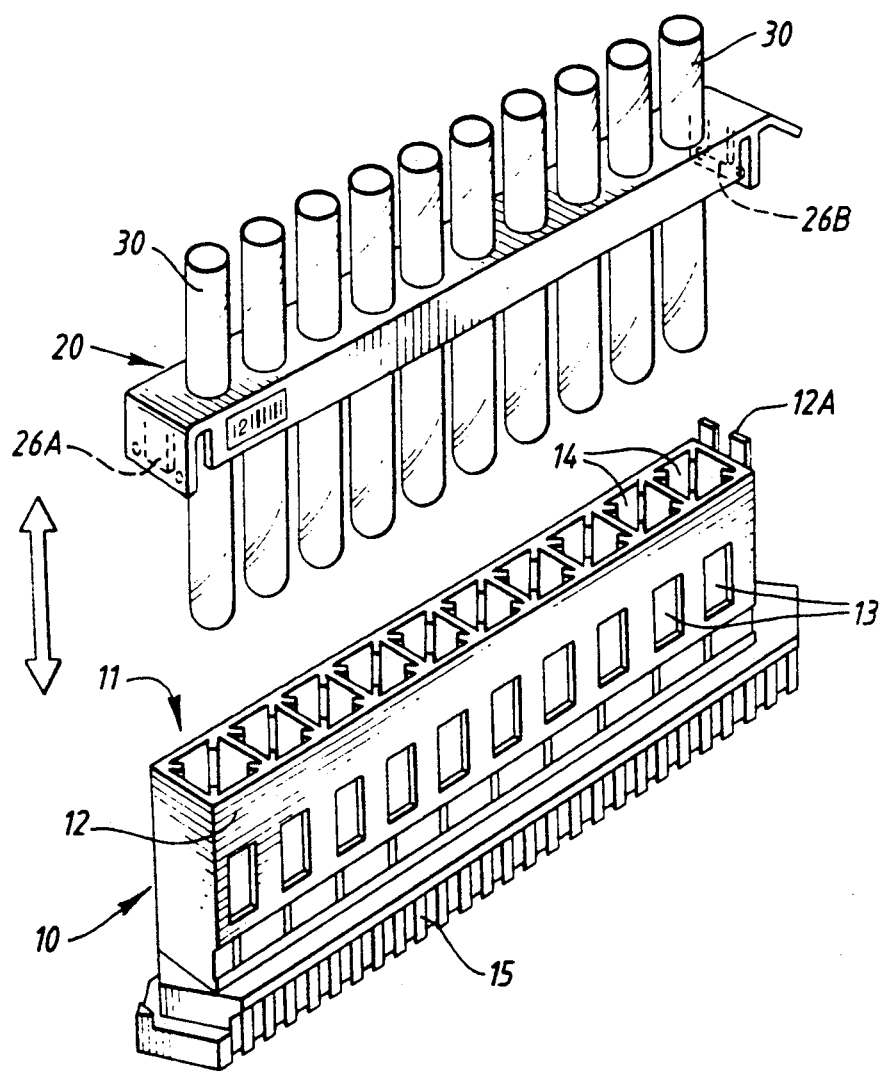
FIG. 4 is an exploded perspective view of a support element with an associated holder according to the invention and with specimen containers inserted.

FIG. 1 shows two of the three essential components of a rack system according to the present invention: a holder 20 for receiving a plurality of specimen containers 30, and a stand 40 for holding a plurality of such holders 20 parallel to one another (see FIG. 3).

Each holder 20 is made of a plastic part 21 which has longitudinal side faces 24A, 24B extending downward along both long sides, and vertical end faces, or extensions, 23A, 23B bent downwardly at both ends of part 21, so that holder 20 has a somewhat trough-shaped form. In the corner regions of part 21, that is at the transitions between side faces 24A, 24B and vertical extensions 23A, 23B, vertical slits 25A, 25B are provided. A handle strip 28 is also attached to one end face.

The design of the vertical extensions 23A, 23B can be seen in detail particularly in FIG. 2. Each vertical extension 23A, 23B, in the lower portion of its middle region, symmetrically to the longitudinal center axis Y—Y of holder 20 (see FIG. 3), has an inwardly pointing thickened portion 26A, 26B, and on both sides of this thickened portion there are respective indentations, indentations 27A being shown at the left-hand end in FIGS. 1-3 and the corresponding indentations at the right-hand end of the holder 20 not being visible in the drawings.

The two vertical extensions 23A, 23B are of equal length, while the thickened portions 26A, 26B extending as far as the lower edge of the extensions are of respectively different widths in the direction between side faces 24A and 24B. Specifically, in the illustrated embodiment, the portions 26B are narrower than the portions 26A.

The stand 40 is in the shape of a U, with a bottom part 40C and two parallel sides parts 40A and 40B. The upper region of stand 40 is especially adapted to holder 20, in order to receive it, as follows:

First, rectangular recesses 40D, 40E are provided on the upper edges of sides parts 40A and 40B, each recess being located between two protrusions, or bosses 41 projecting horizontally by a small distance from parts 40A and 40B. Recesses 40E in the side part 40B are not as wide as the recesses 40D in the left side part 40A.

A horizontal handle strip 48 is attached to the right side part 40B.

The size and shape of recesses 40D, 40E are adapted to the thickened portions 26A, 26B at the interior of holder 20 in such a way that when a holder 20 is placed upon stand 40 the vertical extensions 23A, 23B fit over the side parts 40A, 40B from the outside, and the thickened portions 26A, 26B can then slide into, substantially form-fittingly, an opposed pair of recesses 40D, 40E. At the same time, upwardly projecting regions located at the top of parts 40A and 40B and bordering recesses 40D, 40E nest in slits 25A, 25B. The resulting interfitting relation is particularly clearly seen in FIG. 3. Protrusions 41 then also snap into place in the associated indentations 27A so that a snap-in connection exists between each holder 20 and stand 40.

The aforementioned dissimilar design of the thickened portions 26A and 26B and of the associated recesses 40D and 40E on both sides of the support and holder serve to destroy the symmetry of the holder 20 relative to a central plane parallel to the side parts 40A, 40B of the stand 40, so each holder 20 can be placed absolutely horizontally, i.e., parallel to bottom 40C, upon the stand 40 only in one defined position; conversely, if a mistake is made (for instance if the holder is rotated by 180°), this produces a readily apparent tilted position of the holder 20 on the stand 40, because the (wider) thickened portion 26A on the inside on the left side of a holder 20 cannot be inserted into a (narrower) recess 40E in the right side 40B of the stand 40.

To prevent mistakes from occurring in the first place, the two handle strips 28, 48 are provided on the same side, in the exemplary embodiment on the right side, so that the correct association of the holders 20 in the stand 40 is immediately apparent even without great attention on the part of the user. These provisions accordingly provide double safety against a possible mistaken insertion of holders 20 into the stand 40. Such mistaken placement must absolutely be avoided, because it would cause errors in the order of the specimen containers 30 in the holder 20, and this would have grave consequences both for the outcome of measurement and for the patient involved.

Since, as a function of the particular detection method used and the equipment with which the user works, it may be necessary to remove the holders 20 from the stand 40 and reinsert them a number of times for the various procedures to be performed, this double safety system is of particular significance.

For additional safety and to identify the specimens, a marking strip, for instance a bar code 29, is applied to the side face 24A of the holder 20.

For retaining the specimen containers 30 in the holder 20, the openings 22 on the top of the holder 20 are provided with downwardly oriented elastic plastic tongues 22A, which in the undeformed state, i.e., without a specimen container 30 inserted, point at least slightly inwardly, or in other words are located on the surface of a truncated cone whose axis is perpendicular to the top of plastic part 21. Depending on the outside diameter of the specimen container 30, these elastic plastic tongues 22A are spread apart to a variable extent outwardly upon insertion of a container 30, so that a frictional engagement exists between these tongues 22A and the specimen container 30. Tongues 22A are arranged to make the engagement strong enough that the holder 20 can be transported with specimen containers 30 inserted, without these containers changing their vertical positions in the holder 20.

These plastic tongues 22A also have a centering effect on the specimen containers 30, because they assure a precise vertical alignment of the specimen containers. Both properties have particular significance if the holder 20 carrying the specimen containers is introduced into the support element 10 described in further detail below.

Finally, indentations or bores 49 are formed in the bottom 40C, so that each bore 49 comes to lie vertically below a respective opening 22. The diameter of each bore 49 tapers downwardly so that even specimen containers 30 of different diameters undergo sufficient lateral fixation.

Another factor of significance for cooperation with this support element 10 is the height H of the side parts 40A, 40B of the stand 40; this height H is selected such that with holders 20 mounted as shown in FIG. 3 and with specimen containers 30 inserted through the bores 49 as far as the bottom 40C, containers 30 attain a vertical orientation in the holder 20, which at the same time also assures the proper positioning of the specimen containers 30 relative to measurement openings 13 (FIG. 4) when the holder 20 is mounted on a support element 10.

The bottom 40C of the stand 40 or the bores 49 accordingly serve as a "stop" for the proper introduction of the specimen containers 30 into the holder 20. In addition to having this centering effect, the bores 49 also facilitate the drainage of fluids from the stand, for instance after it has been removed from a water bath.

The third component of the rack system according to the invention, the support element 10, is shown in FIG. 4 along with a holder 20 with specimen containers 30 inserted. This support element 10 substantially comprises a plastic housing 12 which is divided up by transverse walls to form vertical parallel receiving channels 14. The spacing of channels 14 is dimensioned such that a holder 20 can be mounted upon the housing 12 in a manner such that each specimen container 30 will automatically be introduced into the interior of a respective channel 14 of housing 12.

One end face of the housing 12 is formed such that it can engage only with one associated end face of the holder 20, such that the holder 20 holding the specimen containers 30 can be inserted into the support element 10 only in this defined position. This can be effected for instance by means of a postlike extension 12A presenting a recess into which into which the thickened portion 26B of the holder 20 can be fully inserted, while conversely thickened portion 26A of the holder 20 cannot be inserted all the way; once again, if a holder 20 has been mounted incorrectly, the incorrect position of the holder 20 is apparent to the persons using the equipment.

Depending on the type of measurement to be performed (for example, two opposed measuring openings are needed for extinction or fluorescence measurements), measuring openings 13 are provided in one or both side walls of the housing 12, there being in each case one measuring opening 13 in one or each side wall per receiving channel 14. If, as noted above, the specimen containers 30 are inserted properly until they meet the "stop", or in other words until they meet the bottom 40C of the stand 40, then they assume their final position provided for the measurement inside the receiving channel 14 whenever the holder 20 is properly mounted on the housing 12.

Support element 10 is used for transporting a group of specimen containers 30 through the measuring site and to this end, in the preferred embodiment shown, support element 10 has teeth 15 in its lower region, along one longitudinal edge, which can be made to mesh with a toothed belt of a drive unit for each measuring instrument.

Figure 5:
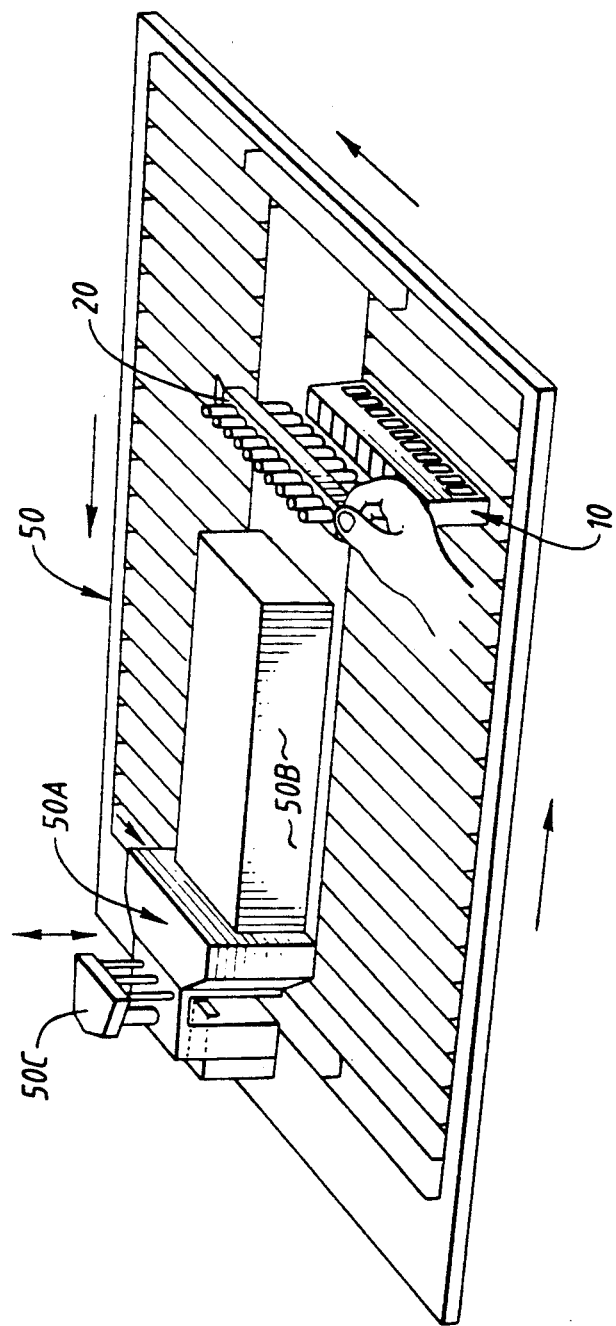
FIG. 5 is a perspective view of the upper receptacle side of a measuring instrument with a support element.

One such measuring instrument 50 is shown in FIG. 5 and includes a measuring site 50A provided with a suitable to drive unit having a toothed belt which will cooperate with teeth 15 to allow continuous transport of a support element 10 through the measuring site 50A of the measuring instrument 50. The design of support element 10 in this lower region in particular, including the provision of,for example, triangular end faces, can be found in the aforementioned U.S. Pat. No. 4,029,961, which also describes the mechanical apparatuses for transporting a plurality of such support elements, and so this mechanism will not be described in further detail here.

FIG. 5 shows the top of such a measuring instrument 50, with only one support element 10, into which a holder 20 carrying specimen containers 30 is being introduced. Support element 10 then travels in the direction of the arrows on the measuring instrument and in so doing moves past the actual measuring site 50A, in which a photomultiplier for detecting chemiluminescence is in particular included, along with an injection device 50C, with the aid of which the reagent that initiates the chemiluminescence is injected into the specimen containers 30. A housing 50B covers the mechanical drive apparatus (motor, toothed belt, guide rollers), and optionally covers part of the photomultiplier as well.

In FIG. 6, the stages of a process typically employed for performing an immunoassay are shown, using the components according to the invention and described in detail above, that is, the holder 20, stand 40 and support element 10.

Figure 6A:
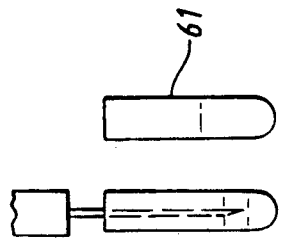
Figure 6B:
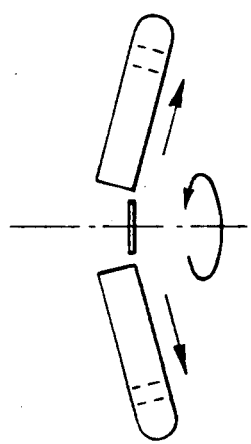
Figure 6C:
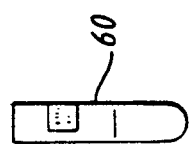

FIG. 6A shows a test tube 60 holding a blood sample which was, for instance, drawn from a patient and containing a substance of interest which is to be detected. In a centrifuging station, the serum used for the measurement and containing the substance to be analyzed, is separated from the blood corpuscles, as shown in FIG. 6B. The serum is removed and a serum sample is usually temporarily stored in the form of a primary sample in a tube 61, as shown in FIG. 6C, for distribution to a plurality of specimen containers for various tests.

Figure 6F:
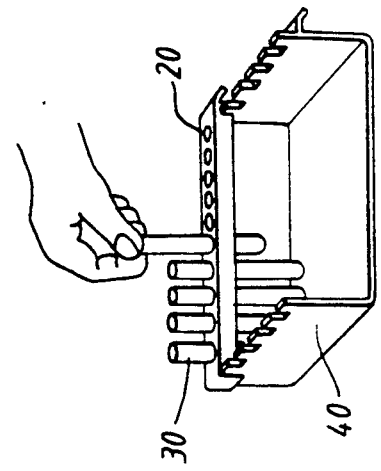
Figure 6E:
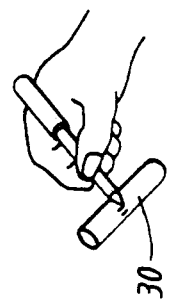
Figure 6D:
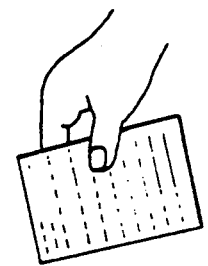

The relevant data such as the name of the patient, type of test, etc., are recorded on a data carrier, depicted in FIG. 6D.

To perform the immunoassay, commercially available specimen containers 30, which may be test tubes, are used and, as shown in FIG. 6E, are provided with a brief identification to match the documentation of FIG. 6D. For certain immunoassays, the specimen containers 30 used here may already be provided with an antibody coating on the inside that is specific for the substance to be analyzed or detected.

As shown in FIG. 6F, the specimen containers 30, suitably prepared and labeled, are then introduced in succession into the holders 20 mounted on a stand 40 and thrust as far as the bottom of the stand 40, where their bottoms plunge into the bores 49 of the bottom 40. Alternatively, a group of specimen containers 30 may already be placed in the holders 20 by the manufacturer of the diagnostic kits. In that case, containers 30 can be written upon very easily, without having to be removed from the holders 20 or replaced therein again after being written upon.

Figure 6I:
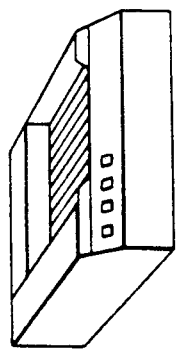
Figure 6M:
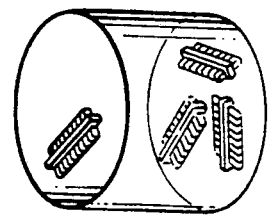
Figure 6H:
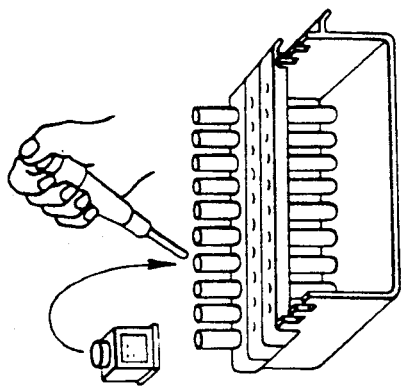
Figure 6L:
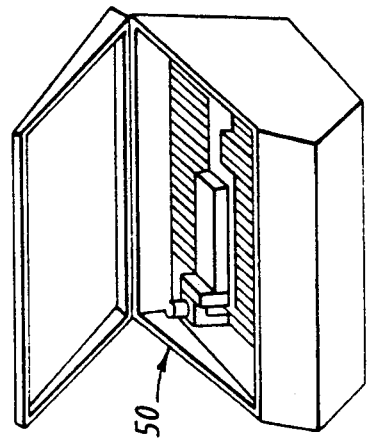
Figure 6G:
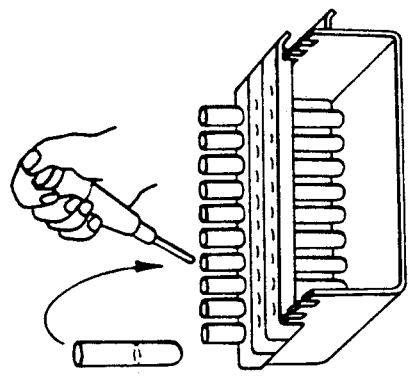

Next, referring to FIG. 6G, the serum in tube 61, taken from the primary sample and containing the substance to be analyzed, is transferred into one of the specimen containers 30, and then the next patient sample is transferred to the next container 30, and so forth, until all of containers 30 for instance contain patient samples. Then the reagents, or in the case of the immunoassay the labeled antibodies or antigens, are introduced with a pipette, as depicted in FIG. 6H. This can either be done while the samples are in stand 40 or one holder after another is removed for adding the reagent and then replaced in stand 40 again.

Next the stand 40, suitably equipped with holders, is introduced into an incubator, shown in FIG. 6I, in which the desired antigen-antibody reaction takes place, optionally at an elevated temperature. To this end it may be necessary, to accelerate the process, to subject stand 40 with the holders 20 to a shaking action.

Figure 6K:
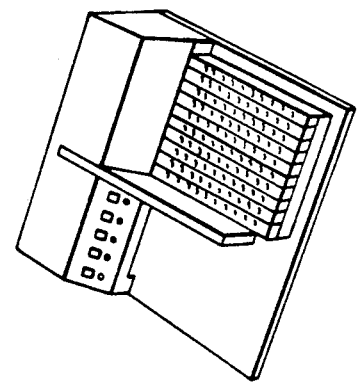

Since if the immunoassay is to proceed properly, excess ingredients in the substances involved must be removed, the stands with the holders are subsequently inserted into a washing apparatus, shown in FIG. 6K. If such equipment is not available in the laboratory, then the specimen containers 30 can be filled with cleaning reagent, and the entire sample rack (stands plus tubes) is decanted. Under some circumstances this part of the procedure may have to be performed several times.

The specimen containers, thus prepared, are then inserted one holder 20 at a time into a support element traveling over a closed path in the actual measuring instrument 50, shown in FIG. 6L, and are then moved past the measuring site, where the substances that initiate the chemiluminescence are added and the resultant light yield is measured, the intensity of which is a standard for the quantity of the substance to be detected in the substance to be analyzed.

After that, the holders, with the specimen containers that have been measured, are removed once again from the associated support element and discarded, as indicated in FIG. 6M.

A special feature of this last step is that in contrast to the previously known methods, the holders 20 can be discarded along with the specimen containers; this represents a major simplification and saves additional steps in the process.

Another significant aspect is that because the specimen containers 30 are firmly retained in the stand 40, secure handling of all containers 30 together becomes possible, for instance while shaking or decanting them, without having to remove individual specimen containers 30 or holders 20.

It is particularly advantageous if the specimen containers 30 are test tubes, for instance with a coating, which are already sold in holders by the diagnostic kit manufacturers, because in that case they can remain in the holders all the way through the process, from the specimen preparation, through the measurement, until they are disposed of.

In immunoassays it is also conventional to bind antigens or antibodies to magnetic (typically paramagnetic) particles that are in suspension. To separate bound and free reagents, external magnets are used to attract the particles in suspension to the inside of the specimen containers, and in this state the fluid with the non-bound reagents can be removed from the test tubes by aspiration or decanting, while the magnetic particles remain in the tubes.

The concept according to the invention of the modular rack, comprising holders 20 and one or more stands 40, can also be advantageously used when magnetic particles are used. It need merely be provided that, for accomplishing the separation and in the actual separating step itself, the specimen containers must be located within the sphere of influence of magnetic fields, while otherwise, for instance during incubation phases, the magnetic field should not have an influence. The stand 40 can therefore be embodied in a known manner in such a way, or with an open bottom surface, that it can be placed on an undercarriage that contains magnets, which after the modular rack is mounted in place exert the magnetic field needed for the separation upon the magnetic particles located in the suspension. The magnets, generally permanent magnets, are disposed in such a way that they attract the magnetic particles either toward the bottom or, in the lower region, to the sides of the specimen containers.

For decanting, the combination of the holders, stand and undercarriage is then tipped over as a unit.

After that the combination of holders and stand can be disconnected from the undercarriage again, and washing fluid, for instance, may be added. The holder and stand combination can then be mounted on the undercarriage again; a period during which the magnetic particles deposit on the wall can be waited out, and then decanting can be performed again.

This application relates to subject matter disclosed in Federal Republic of Germany application P 38 36 163.9-52, filed on Oct. 24, 1988, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A system for holding a plurality of specimen containers, during performance of assays which are constituted by a sequence of procedures including a measurement procedure, in a measuring instrument having a measuring site at which the measurement procedure is performed, said system comprising: a support element specifically constructed to cooperate with the measuring instrument for moving the specimen containers successively past the measuring site; and a holder for holding a group of the specimen containers in a row, said holder comprising a plastic part having a longitudinal axis and provided with a group of container receiving openings spaced apart along said longitudinal axis for frictionally receiving the group of specimen containers, said plastic part having means for mounting said holder upon said support element in a defined position relative to said support element, wherein:

said support element comprises a housing having a longitudinal dimension, a top, a bottom and a group of receiving channels extending between said top and said bottom, opening at said top and spaced apart along said longitudinal dimension, each said receiving channel being provided with a respective lateral measuring opening disposed at a location between said top and said bottom;

said channels are oriented and dimensioned to receive specimen containers held by said holder when said holder is mounted in said defined position upon said support element so that each specimen container will be in a defined position relative to an associated channel such that a region of each specimen container will be in registry with a respective lateral measuring opening;

a stand for receiving a plurality of said holders outside the measuring instrument;

said holder is a bracket-like disposable component in which a group of specimen containers can remain during all of the assay procedures, including the measurement procedure; and said stand having two vertical side parts and a horizontal base part extending between said side parts to give said stand a U-shaped cross section, each said side part having a top edge which is remote from said base part and which is provided with a plurality of recesses, said recesses being dimensioned such that a plurality of said holders can be placed parallel to one another upon said stand, each said recess being constructed such that each holder engages in a respective recess in each side part for maintaining each holder in a defined position relative to the said stand.

2. The system of claim 1 wherein the measuring instrument has a drive mechanism including a toothed belt at the measuring site and said housing is provided with teeth located adjacent said bottom regions for cooperating with the toothed belt during a measurement procedure.

3. The system of claim 1 wherein said holder has a top surface extending parallel to said longitudinal axis, each said container receiving opening is provided with downwardly pointing elastic plastic tongues which coincide with a conical surface when no specimen container is disposed therein, the conical surface having an axis which is perpendicular to said top surface, and said tongues being located to be spread apart upon the introduction of a specimen container in a respective container receiving opening.

4. The system of claim 1 wherein said holder has a U-shaped cross section in the plane at right angles to said longitudinal axis.

5. The system of claim 1 wherein said holder has a handle strip at one of its ends.

6. The system of claim 1 wherein said plastic part has two end faces which are spaced apart in the direction of said longitudinal axis and which constitute two vertical extensions each perpendicular to said longitudinal axis and each located at a respective one of said end faces.

7. The system of claim 6 wherein said plastic part has a top surface extending parallel to said longitudinal axis and two longitudinal side faces extending between said end faces and perpendicular to said top surface, said top surface and said side faces forming a U-shaped cross section in the plane at right angles to said longitudinal axis, and said plastic part is provided with vertical slits formed between said vertical extensions and said side faces.

8. The system of claim 6 wherein said plastic part has a top surface extending parallel to said longitudinal axis, each vertical extension has two lateral edges extending perpendicular to said longitudinal axis and a lower edge remote from said top surface, and each vertical extension has a thickened portion at the side of said vertical extension which faces the other end face of said plastic part, in the vicinity of said lower edge and spaced inwardly of said lateral edges.

9. The system of claim 8 wherein each said vertical extension is provided with two indentations at the side of said vertical extension which faces away from the other end face of said plastic part, each said indentation being disposed adjacent a respective one of said two lateral edges of said vertical extension.

10. The system of claim 8 wherein:

said plastic part has a top surface extending parallel to said longitudinal axis and two longitudinal side faces extending between said end faces and perpendicular to said top surface, said top surface and said side faces forming a U-shaped cross section in the plane at right angles to said longitudinal axis, and said plastic part is provided with vertical slits formed between said vertical extensions and said side faces; and each of said recesses in said top edge of each of said side parts is of rectangular cross section, and the spacing between, and cross section of, said recesses are such that a plurality of said holders can be placed parallel to one another upon said stand with said thickened portions engaging in said recesses, said vertical extensions fitting, over and disposed outside of, said side parts, and portions of said side parts bordering said recesses seated said slits.

11. The system of claim 10 wherein said stand has a handle strip extending from at least one of said side parts.

12. The system of claim 10 wherein the height of said side parts, perpendicular to said base part, is dimensioned such that when the specimen containers are seated on said base part, the positions of the specimen containers within said holder is such that when said holder is subsequently mounted upon said support element, the specimen containers extend into said receiving channels to a point at which the specimen containers assume the defined position relative to their associated lateral measuring openings.

13. The system of claim 10 wherein:

each said vertical extension is provided with two indentations at the side of said vertical extension which faces away from the other end face of said plastic part, each said indentation being disposed adjacent a respective one of said two lateral edges of said vertical extension; and each said side part is provided with outwardly directed protrusions adjacent each side of each said recess in correspondence with said indentations in said vertical extensions of said plastic part for establishing a detent connection between said holder and said stand.

14. The system of claim 10 wherein said thickened portions of said vertical extensions and said recesses in said side parts are formed asymmetrically with respect to a median plane midway between, and parallel to, said side parts to an extent such that a parallel positioning of said holder with respect to said base part of said stand is possible only for one defined position of said holder relative to said stand.

15. The system of claim 14 wherein said thickened portions of said vertical extensions and the associated recesses in said side parts of said stand correspond to one another in pairs.

16. The system of claim 10 wherein said base part of said stand has a plurality of bores located to each be under a respective container receiving opening of said holder when said holder is mounted on said stand.

17. The system of claim 16 wherein each of said bores tapers downwardly.

18. The system of claim 1 wherein said plastic part has two longitudinal side faces extending parallel to said longitudinal axis and further comprising an identification element applied to the one of said side faces.

19. The system of claim 18 wherein said identification element is a bar code strip.

* * * * *